United States Patent [19]

Alsop

[11] 3,981,777
[45] Sept. 21, 1976

[54] METHOD AND APPARATUS FOR TESTING MATERIALS FOR LEVELS OF AGENTS INHIBITORY OR TOXIC TO MICROORGANISMS

[75] Inventor: George Michael Alsop, South Charleston, W. Va.

[73] Assignee: Union Carbide Corporation, New York, N.Y.

[22] Filed: Jan. 19, 1976

[21] Appl. No.: 650,356

[52] U.S. Cl.......................... 195/103.5 R; 195/127; 195/139
[51] Int. Cl.² ........................................... C12K 1/00
[58] Field of Search............... 195/103.5 R, 127, 139

[56] References Cited
UNITED STATES PATENTS

| | | | |
|---|---|---|---|
| 2,990,339 | 6/1961 | Frank et al. | 195/103.5 R |
| 3,504,185 | 3/1970 | Zweig et al. | 195/103.5 R |
| 3,751,340 | 8/1973 | Witz | 195/103.5 R |
| 3,846,243 | 11/1974 | Fletcher | 195/103.5 R |
| 3,881,993 | 5/1975 | Frecke et al. | 195/127 |

*Primary Examiner*—A. Louis Monacell
*Assistant Examiner*—Robert J. Warden
*Attorney, Agent, or Firm*—Eugene Lieberstein

[57] ABSTRACT

Method of and apparatus for testing materials for levels of agents that are toxic and/or inhibitory to microorganisms involving (a) the mixing of a sample of said material with a liquid medium containing microorganisms, said medium being capable of supporting growth of said microorganisms; (b) the impregnating of the resulting liquid mixture into a porous inert support mass capable of permitting oxygen transfer from ambient gas enveloping said mass to said mixture impregnated into it; (c) the incubating of said mixture impregnated into said mass for a period of time and under conditions sufficient to promote bacterial growth therein in the absence of toxic or inhibitory agents; (d) the removing of the incubated mixture from said inert support mass and filtering same through an open pore filter; and (e) the observing of the degree of turbidity, or lack of it, in the resulting filtrate. In particular, the apparatus of the invention comprises (1) a plurality of closed test reactors; (2) a porous inert support mass disposed within each said reactor and capable of being impregnated with a liquid test mixture and permitting transfer of oxygen from ambient oxygen-containing gas enveloping said mass to said mixture; and (3) a closed source of oxygen connected to said closed test reactor to provide oxygen thereto.

11 Claims, 2 Drawing Figures

METHOD AND APPARATUS FOR TESTING MATERIALS FOR LEVELS OF AGENTS INHIBITORY OR TOXIC TO MICROORGANISMS

BACKGROUND OF THE INVENTION

1. Field of the Invention

The invention relates to a method of and apparatus for testing materials, such as microbiological growth control agents for paper mill streams or cooling waters, or waste intended for biological treatment to determine whether or not such materials are effective in inhibiting or preventing growth of microorganisms. The method and apparatus of this invention directly compare the actual effect of a sample of the waste on the growth of microorganisms as measured by the turbidity or lack of same in liquid mediums containing them. In the present invention, turbidity indicates growth whereas clearness or lack of turbidity indicates the presence of materials inhibitory or toxic to the growth of microorganisms. The present invention also provides means for ensuring against false microorganism growth indications because of turbidity from precipitates which might form from possible reaction of the test sample of waste with one or more components of the medium or which might form from any of components of the medium or inter-reaction of two or more such components.

2. Description of the Prior Art

Biological waste treatment involves the oxidation of chemical compounds by active microorganisms to innocuous end products. Both the rate and the extent of oxidation are dependent upon the "health" of the microorganisms and the various characteristics of the influent waste. A common method for treating sewage to remove pollutants is by the activated sludge process. According to this process, the sewage, with or without primary clarification, is thoroughly mixed with oxygen-containing gas in the presence of aerobic bacteria in a lagoon of active microorganisms commonly called a secondary treatment lagoon. The organic matter contained in the sewage is absorbed and biologically oxidized by the bacteria. Subsequently, the bacteria are separated, e.g., by gravity settling, the purified effluent is decanted and discharged into a receiving stream or body of water with or without prior disinfection with chlorine or ozone.

The problems encountered in treating industrial wastes are more complex, especially in the secondary treatment, than with domestic wastes. Some synthetic industrial compounds produced by or used in process units are inhibitory to the respiration of the biological microorganisms in the secondary waste treatment unit. Therefore, the detection of the presence of potentially inhibitory or toxic materials in the waste before the waste reaches the secondary unit is preferred to protect the microorganisms in the secondary treatment units from large concentrations of highly toxic materials. Control of these potential upsets is required to avoid severe damage to the secondary treatment lagoon, to avoid pollution of the stream or body of water receiving the effluent from the secondary treatment lagoon, and so that the treatment plant can conform to public waterway discharge permits. Inhibitory materials can be low to high concentrations of potentially toxic compounds. In the case of inhibitory or toxic compounds, a percentage of the biological organisms may be killed or inhibited, thus reducing the efficiency of the secondary biological waste treatment or even rendering it ineffective.

In order to effectively treat a waste biologically a number of its characteristics must be known. Among these characteristics is the presence of materials that affect biological growth, e.g., toxic compounds. Often a waste that is toxic can be treated by the application of a detoxification step prior to biological treatment. Another approach is to eliminate the toxicant at its source and treat by an alternative means. A very integral part of any study related to toxicity, be it detoxification or point source identification, is the toxicity evaluation test. The purpose of the toxicity evaluation test is to ascertain a material's toxic impact on the biomass (microorganisms).

Most biomass toxicity tests in current use in regard to water pollution control processes, are based on a measurement of the biological oxygen consumption. Such tests have proven to be insensitive in some cases, because, although a particular biomass may not be capable of growth, it can still show an oxygen uptake. This is apparently true since oxygen uptake measurements are taken over periods of time where growth may not necessarily be the result of oxygen consumption. In any event, the real question of toxicity, with respect to biological treatment, should be whether the biological system will sustain growth rather than will it show an oxygen uptake.

Furthermore, previous attempts to protect the secondary treatment unit took the form of BOD detection systems inside the primary or secondary treatment boundaries. As a consequence, any abnormal influent waste conditions were detected too late in many cases for correction or diversion. Commercially available oxygen uptake monitors are typically installed in the biobasin and measure the respiration of the biomass after influent waste water has been pumped into the aerobic biological basin. No really effective positive corrective measures can be initiated at this point and it is usually too late to avoid damage and loss. Examples of prior art which measure the respiration of the biomass after the influent waste water has been pumped into the aerobic biological basin include U.S. Pat. Nos. 3,342,727; 3,348,409; 3,426,899; 3,510,407; 3,557,954; 3,731,522 and 3,740,320. U.S. Pat. No. 3,684,702 describes a laboratory technique for determining toxic sewage waters wherein one analysis fermenter is continually supplied with sewage water, bacteria and additional nutrient while a second analysis fermenter contains only bacteria and the additional nutrient. if the oxygen consumption per time unit is smaller in the first fermenter than in the second, an impediment or poisoning of the bacteria is stated to exist, as a result of which alarms are sounded or countermeasures are taken. However, the waste water is already at the secondary unit leaving essentially no time for corrective measures and it is not always accurate to assume that the oxygen uptake results from biological growth.

Other prior art such as U.S. Pat. Nos. 2,990,339; 3,014,848; 3,255,095; 3,474,001; 3,504,185; 3,714,445; 3,730,842; and 3,832,532 illustrate the well known expedient of measuring turbidity, optical density or light scattering ability as indicators of microorganism population. None of the patents mentioned above, however, disclose or suggest the incubating on a porous inert support mass of a mixture of a sample of the material being tested with a liquid medium containing microorganisms and capable of supporting growth of the microorganisms, removing and filtering the mixture and observing its turbidity.

Furthermore, no prior art is known which discloses, teaches or suggests a method of or apparatus for measuring the actual effect of industrial sewage or other liquid waste on the health, vigor or growth potential of microorganisms in the manner described herein.

SUMMARY OF THE INVENTION

The present invention provides an apparatus and method that will detect the above-mentioned toxic conditions in waste materials that are injurious to microorganisms. The method of the present invention permits the testing of a material to be subjected to treatment by microorganisms in a waste treatment facility to detect the presence or absence of toxic agents capable of injuring said microorganisms and comprises the steps of (1) mixing a sample of said material with a liquid medium containing microorganisms, said medium being capable of supporting growth of said microorganisms; (2) impregnating the resulting liquid mixture into a porous inert support mass capable of permitting oxygen transfer from the ambient gas enveloping said mass to said mixture impregnated into it; (3) incubating said mixture impregnated into said mass for a period of time and under conditions sufficient to promote bacterial growth therein in the absence of toxic agents; (4) removing the incubated mixture from said inert support mass; (5) filtering same through an open pore filter; and (6) observing the degree of turbidity, or lack of it, in the resulting filtrate. The liquid medium can contain domestic sewage as a source of microorganisms as well as nutrients for the microorganisms, a buffer and a microbiological growth substrate. The source of microorganisms can be a nutrient broth which also provides nutrients or can be the solids obtained by filtering and washing domestic sewage.

Unlike other toxicity tests based on oxygen consumption assumed to be the consequence of microbiological growth, the biomass toxicity test of this invention measures actual microbiological growth or lack or it. It has been found that turbidity due to bio-growth carried out on a porous inert support mass, e.g., glass wool, in an oxygen atmosphere (or lack of such turbidity) can be related to biomass toxicity within a relatively short period of time using a simple appartus that can be made portable. The measurement of turbidity as an indicator of microorganism population has been used over the years by microbiologists. The apparatus and method of this invention uses this principle in an efficient manner to measure biological growth in a meaningful and reliable way. The test of this invention can be conducted using a compact kit described herein. Data can be generated quickly at low cost and the data are meaningful in terms of their relationship to biological treatment systems.

More particularly, the carrying out of the biogrowth on the porous inert support allows sufficient oxygen transfer without direct aeration. This arrangement minimizes the loss of volatile organics and simplifies the required equipment. The inert support is saturated with a mixture of (1) a source of microorganisms, such as, settled domestic sewage, or a nutrient broth, (2) nutrients, (3) a buffer, and (4) a microbiological growth substrate to which has been added the sample of material being tested at full strength and various dilutions. The degree of toxicity can be assessed from observations of filtrates after a period of microbiological growth.

The biomass is then incubated for a period of time sufficient to permit bio-growth unless inhibited, e.g., for 16 hours. The inert support is then squeezed to remove the liquor and the liquor is filtered through an open-pore filter to remove flocculated biomass, since toxicants will normally cause the initial biomass to flocculate. The open-pore filter removes any flocculated biomass and allows dispersed growth to pass through with the filtrate. The test mixtures, containing no problem materials at a toxic level will contain dispersed growth that passes through the filter yielding a turbid filtrate. Thus, toxicity can be detected by the naked eye by looking for turbidity in the full strength mixture and the various dilutions. Materials that are toxic yield clear filtrates. The degree of toxicity can be assessed from the observations at the various dilutions of the test material. This approach can be incorporated into a portable field test kit which is readily transportable from place to place in the field in an attache-size carrying case.

The present invention also provides various controls to rule out false results. These controls are preferred, not essential, and are carried out simultaneously with the testing of the waste sample. The first control test, suitably called the "growth support control test," can be conducted to ensure that the medium employed to support the growth of the microorganisms does in fact do so. In the first control test the method of the invention is carried out in the manner described above except that an equal amount of water is used in place of the sample of waste material being tested. If turbidity results, growth has taken place and the medium and conditions used can be concluded to be capable of supporting the growth of microorganisms. If a clear filtrate results, growth has not taken place and the medium and/or conditions used can be suspected of not supporting growth and the concurrent test results on the waste sample can be rejected.

Another control test, aptly called the "reagentwaste sample control test," can be conducted to ensure that no component of the sample of waste material or any other substance in the mixture reacts to form a turbid filtrate which could falsely indicate microbiological growth when there was none. This control test entails the addition to the growth medium (which also contains the waste sample being tested) of a reagent having known toxicity to the microorganism and being incapable of reaction with any ingredient of said medium to form a turbid filtrate. The known toxic reagent is added in an amount sufficient to inactivate any microorganisms present in the medium. A clear filtrate is obtained when the waste sample contains no component capable of reacting with any ingredient of the medium to form a turbid filtrate. A turbid filtrate would result from other than microbiological growth and would suggest a malfunction because of a precipitate-forming reaction in the system.

A third control test, which can be called the "reagent-medium control test," can be carried out to ensure that no component of the medium reacts or interreacts with other components to form a turbid filtrate which could falsely indicate microbiological growth when there was none. This control test entails the substitution of an equal amount of water in place of the waste sample being tested. Then, a reagent having known toxicity to the microorganism is added to the medium which does not contain any waste sample. The reagent is incapable of reaction with any ingredient in said medium to form a turbid filtrate and is added in an amount sufficient to inactivate any microorganisms present therein. A clear filtrate is obtained when the medium contains no ingredient capable of reacting with any other ingredient or the reagent to form a turbid filtrate. A turbid filtrate would result from other than microbiological growth and the concurrent test results on the waste sample could then be rejected.

Apparatus of the present invention comprises a plurality of closed test reactors, such as square stoppered bottles. A porous inert support means, e.g. glass wool, is disposed within each reactor and is capable of being impregnated with a liquid test mixture and permitting transfer of oxygen from ambient oxygen-containing gas enveloping the mass to the mixture. A closed source of oxygen, e.g., a cylinder of oxygen, is connected to each said closed test reactor to provide oxygen thereto. A manifold connects the closed source of oxygen to said closed test reactors to supply oxygen thereto. A pressure regulator is connected to the closed test reactors for maintaining a pressure therein slightly above ambient atmospheric pressure. The method of this invention does not have to be carried out in apparatus of this type; for example, the test reactors can be open to the atmosphere and draw oxygen therefrom. It is preferred, however, to avoid the possibility of oxygen-starved conditions and to promote rapid growth by the use of oxygen. Also, when the test and control mixtures are open to the atmosphere there may be some possibility of external contamination of or other interference with some but not all mixtures which could provide misleading results.

DESCRIPTION OF A PREFERRED EMBODIMENT

Figure 1:
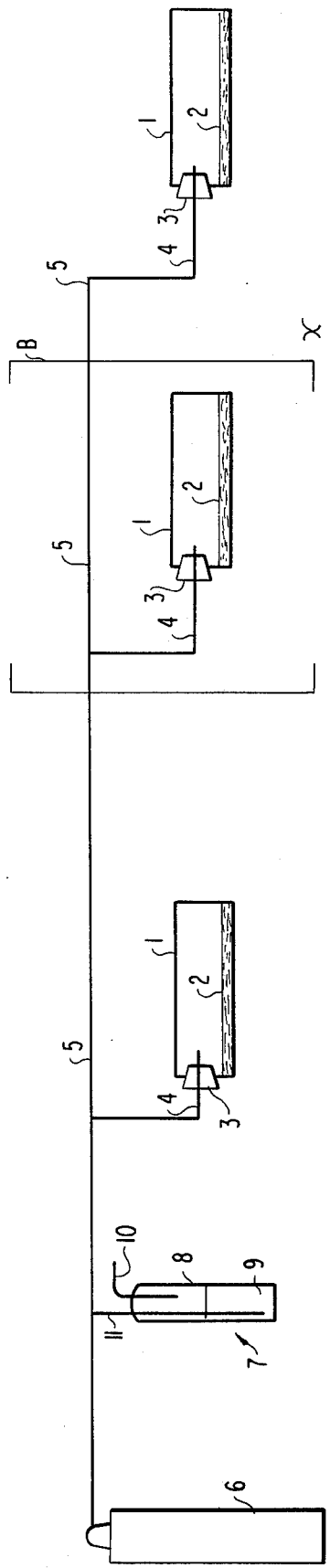
FIG. 1 is a diagrammatic view illustrating an embodiment of the apparatus of this invention.

In FIG. 1, a plurality of reaction vessels or test reactors 1 are provided with mats of porous inert support mass 2. Each test reactor 1 is closed with a stopper 3 through which tube 4 passes. Each tube 4 is connected to a manifold 5 which, in turn, is connected to a source of oxygen such as an oxygen cylinder 6. The manifold 5 is also connected to pressure regulator 7 which includes a closed vessel 8 containing a liquid 9, e.g., water, a vent 10 through the top wall of the vessel 8 to vent the interior of the vessel 8 to the atmosphere and a pipe 11 connected to the manifold 5 and extending below the surface of the liquid in the vessel 8. The pressure regulator 7 maintains the pressure of oxygen in the manifold at slightly above the ambient atmospheric pressure. The brackets B and subscript X shown in the figure indicate additional repeating units of test reactors 1, mats 2, stoppers 3 and tubes 4 to the manifold 5. The subscript X designates an integer from 0 to 20 or more which would include 2 to 22 or more of the test reactors 1. More test reactors 1 can be used if desired, in which case the integer X may be higher than 20. Sixteen test reactors 1 have been found to be a convenient number.

Figure 2:
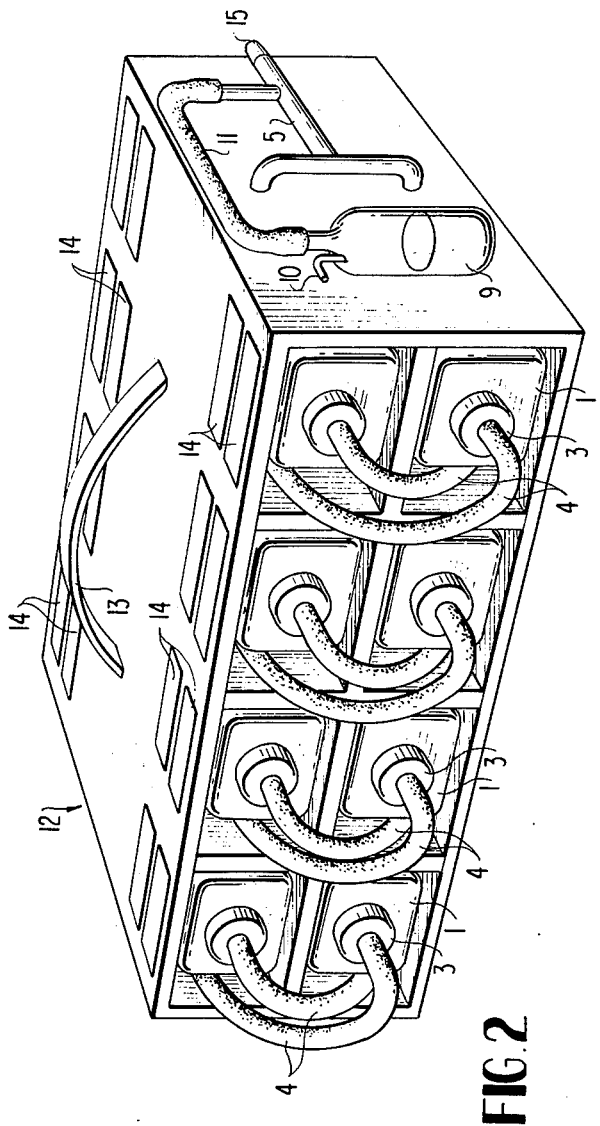
FIG. 2 is a perspective view of the embodiment shown in FIG. 1 mounted in a portable rack or holder.

It is also quite advantageous to mount, as shown in FIG. 2, the test reactors containing the inert porous support mass in a rack or holder 12 which also mounts the manifold 5, tubes 4 and the pressure regulator 7. The rack is of suitable size that it fits into an attache case or other small-sized hand-carrying case. The rack or holder 12 is provided with a carrying handle 13 and label plates 14 fixed to its top surface for identifying each reactor 1. The end 15 of manifold 5 is adapted to be connected to a source of oxygen such as an oxygen cylinder or bottle. In the particular instance shown in FIG. 2, the rack 12 is adapted to hold sixteen test reactors 1. The carrying case for the rack 12 is sufficiently large to also contain the necessary reagents as described hereinafter and the open pore filter paper, holder therefore, vials or test tubes, syringes, spatulas, volumetric glassware and other miscellaneous equipment useful in carrying out the testing procedure.

The inert porous support mass is conveniently glass wool which is inert to the reagents, test mixture and conditions used in the method of this invention. However, any other such inert materials can be used. It is probable that various types of stainless steel wools can be used as well as certain chemically and microbiologically resistant plastics. It is also possible to employ mineral products such as rock wool and the like. Any fibrous or porous material can be used, and preferably is characterized by the inertness described above. Whatman No. 4 filter paper is a suitable open pore filter and many other suitable types of filter paper are available and can be used in place of Whatman's No. 4 filter. As an illustration of filters that can be used, it is preferable that the filter permit passage of particles of roughly 100 microns or less, most preferably roughly 20 microns or less, and retain larger particles.

In a preferred embodiment the waste material being tested is tested at several concentrations in a mixture containing microorganisms, nutrients and growth substrate. The mixture is incubated for a suitable period, e.g., about 16 hours, on the porous inert support 2 in an oxygen atmosphere. After the mixture has been incubated the inert support is squeezed and the liquor is passed through an open pore filter. The open-pore filtration removes the flocculated biomass and allows dispersed growth to pass through with the filtrate. The waste material tested free of problem substances at a toxic level will contain dispersed growth which is evident by a turbid filtrate. Materials that are toxic will yield a clear filtrate. The "degree" of toxicity can be assessed from the observations of the turbidity levels of the waste material at the various concentrations. A positive result (non-toxic) does not necessarily mean that the waste material will support bio-growth, since the test mixture contains a growth substrate and growth will occur even if the waste material tested is nonbiodegradable.

The microorganisms can be obtained from any suitable source, e.g., domestic sewage and nutrient broth such as Bacto-nutrient broth. The Bacto-nutrient broth is a dry powder making it an easily transported and a readily available source of microorganisms. Also the Bacto-nutrient broth contains the necessary trace nutrients eliminating several nutrient solutions required when domestic sewage microorganisms are used.

Two test methods A and B have been developed and are described hereinafter.

METHOD A

The following reagents are prepared:

a. Magnesium sulfate solution: 2.3 grams of $MgSO_4.7H_2O$ dissolved in 100 ml of water.

b. Calcium chloride solution: 2.8 grams of $CaCl_2$ dissolved in 100 ml of water.

c. Ferric chloride solution: 25 mg of $FeCl_3 \cdot 6 H_2O$ dissolved in 100 ml of water.

d. Ammonium chloride solution: 170 mg of $NH_4Cl$ dissolved in 100 ml of water.

e. Sodium acetate (growth substrate) solution: 0.6 gram of sodium acetate dissolved in 100 ml of water.

f. Domestic sewage: Settled domestic influent that has been filtered through a glass wool plug.

g. Phosphate buffer solution: 850 mg of $KH_2PO_4$, 2.18 grams $K_2HPO_4$, and 1.77 grams $Na_2HPO_4$ dissolved in 100 ml water.

h. Sulfuric acid solution: 10 ml of concentrated $H_2SO_4$ slowly added to 80 ml of water, allowed to cool and brought to a volume of 100 ml.

i. Sodium hydroxide solution: 10 grams of NaOH dissolved in 100 ml of water.

j. Cyanide solution: 0.25 gram of KCN dissolved in 100 ml of water. Cyanide is a toxic substance and extreme care should be taken when handling.

Distilled water or ion exchanged water is used throughout. A mixed nutrient solution is prepared by mixing equal volumes of the above-identified solutions of magnesium sulfate (a), calcium chloride (b), ferric chloride (c), and ammonium chloride (d). The mixed nutrient solution should be made up just prior to use so as to avoid precipitation problems.

The pH of the sample of waste material to be tested is adjusted to the range of 6 to 8, if it is not already in that range, using the sodium hydroxide solution (i) or sulfuric acid solution (h) identified above. The sample is tested in four dilutions prepared as follows:

TABLE I

| Test Sample Dilution Designation | Test Sample Dilution | Test Sample Dilution Preparation |
| --- | --- | --- |
| 0-S | Full strength | Full strength sample |
| 1-S | 1/10 | 1 ml of 0-S plus 9 ml of water |
| 2-S | 1/100 | 1 ml of 1-S plus 9 ml of water |
| 3-S | 1/1000 | 1 ml of 2-S plus 9 ml of water |

In addition to the above test sample dilutions, control sample dilutions that contain a toxic concentration of cyanide, for control purposes are prepared as follows:

TABLE II

| Control Sample Dilution Designation | Control Sample Dilution | Control Sample Preparation |
| --- | --- | --- |
| 0-CN | Full strength | Full strength sample containing 0.25 gram KCN per 100 ml |
| 1-CN | 1/10 | 1 ml of 0-CN plus 9 ml of cyanide solution identified above as reagent (j) |
| 2-CN | 1/100 | 1 ml of 1-CN plus 9 ml of said cyanide solution |
| 3-CN | 1/1000 | 1 ml of 2-CN plus 9 ml of said cyanide solution. |

The above-described dilutions are conveniently made by the use of syringes and small vials although any suitable utensils and containers may be used. It is important, however, to isolate those vials and syringes that have been contacted by cyanide solutions from the other non-cyanide solutions.

To each of 16 vials there are added 10 ml of domestic sewage (f), 5 ml of sodium acetate solution (e), 2 ml of phosphate buffer solution (g) and 0.3 ml of the mixed nutrient solution. The following additions, in the amount of 2 ml each, are made to the vials as indicated in Table III below.

TABLE III

| Vial Number | Additions |
| --- | --- |
| 1 | Water |
| 2 | Water |
| 3 | 3-S |
| 4 | 3-S |
| 5 | 2-S |
| 6 | 2-S |
| 7 | 1-S |
| 8 | 1-S |
| 9 | 0-S |
| 10 | 0-S |
| 11 | 3-CN |
| 12 | 2-CN |
| 13 | 1-CN |
| 14 | 0-CN |
| 15 | Cyanide solution (j) |
| 16 | Cyanide solution (j) |

The apparatus shown in FIG. 1 is used wherein 16 test reactors 1 are provided, i.e., x is 14. Each of the above solutions in vials nos. 1 through 16 is poured into a corresponding test reactor 1 (with corresponding numbers) in such a manner that the solution is absorbed on the glass wool mat 2 which weighs about 1 gram. The test reactors 1 are then connected to the oxygen manifold 5 and allowed to incubate at room temperature (20°–25°C) for approximately 16 hours. Thereafter the test reactors 1 are removed from the oxygen manifolds 5. Using a spatula the glass wool mat is worked to the neck of the test reactor 1 and the liquor in the mat is squeezed from the mat into a Whatman No. 4 filter. The liquor is allowed to gravity filter through the Whatman filter into a numbered vial.

The filtered liquor in the vial is examined for turbidity using the naked eye or the apparent absorbence is measured at 530 nm using a spectrophotometer (such as Spectronic 20, Beckman) and distilled or ion exchanged water for the blank.

Bottles nos. 1 and 2 provide a "growth control." This control indicates whether the system is capable of producing a viable population of microorganisms. The control is run in the same manner as the test samples (e.g. 0-S, 1-S, 2-S, 3-S) with the exception that an equal amount of water is substituted for the test sample of waste material. For the test to be valid this control must yield a turbid filtrate.

Bottles nos. 11–14 provide a "reagent-sample control." This control indicates whether there is any component or components in the test sample of waste material that can react with the reagents (a) through (j) to yield a turbid filtrate. This control is run in the same manner as the test samples (0-S, 1-S, 2-S, 3-S) at the various dilutions with the exception that sufficient cyanide is added to the test materials to inactivate any microorganisms in the testing system. These controls must yield clear filtrates for the test to be valid.

Bottles nos. 15 and 16 provide a "biomass background - reagent control." This control is carried out in the same manner as the growth control with the exception that sufficient cyanide solution (j) is added to inactivate the microorganisms. This control indicates whether any of the components of the test system components in the above of the source of microorganisms can yield a turbid filtrate. This control must yield a clear filtrate for the test to be valid.

METHOD B

The sodium acetate solution (e) phosphate buffer solution (g), sulfuric acid solution (h), sodium hydroxide solution (i) and cyanide solution (j) identified hereinabove in respect to Method A are reagents for Method B as well. In addition, a nutrient broth/sodium acetate solution (k) is prepared by dissolving 0.8 gram of Bacto-nutrient broth and 0.6 gram of sodium acetate in 100 ml of distilled water. Distilled water or ion exchanged water is used throughout. No mixed nutrient solution or domestic sewage are required as they are in Method A.

The pH of the sample of waste material to be tested is adjusted as described in Method A. Also, the test sample is tested in the four dilutions as given in Table I. Control sample dilutions as described in Table II are also prepared and tested.

To each of 16 vials there are added 5 ml of the nutrient broth/sodium acetate solution (k) prepared as described above. In addition, 2 ml of the phosphate buffer solution (g) and 10 ml of distilled water are added. Thereafter, 2 ml of the dilutions prepared pursuant to Tables I and II are added to the respective vials the contents of which are respectively identified in the same manner as set forth in Table III.

The apparatus shown in FIG. 1 is used in the same manner as is described hereinabove for Method A. The "growth control," (Bottles nos. 1 and 2), the "reagent-sample control" (Bottles nos. 11–14), and the "biomass background-reagent control" (Bottles nos. 15 and 16) provide indications of validity or invalidity of the tests in the same manner as described hereinabove in respect to Method A.

Any reaction, with the exception of aerobic growth, that yields a turbid filtrate is to be avoided.

The microorganisms can be obtained from several different sources; two method options related to microorganism source being domestic sewage and nutrient broth, e.g., Bacto-nutrient broth. The Bacto-nutrient broth is a dry powder making it an easily transported and a readily available source of microorganisms. Also the Bacto-nutrient broth contains the necessary trace nutrients eliminating the need of the several nutrient solutions required when domestic microorganisms are used.

The method and apparatus were tested on synthetic and actual samples. The following observations were obtained using domestic sewage as a source for microorganisms and synethic samples, i.e., crotonaldehyde solutions and potassium cyanide solutions. In each instance, the aqueous solutions of crotonaldehyde and potassium cyanide identified in the first column of Table IV below were made up and used as the sample waste material in Method A. The result in each instance is given in the second column of Table IV.

TABLE IV

| Crotonaldehyde Concentration (mg/l) | Filtrate Character (Visual Observation) |
|---|---|
| 1 | Turbid |
| 10 | Clear |
| 46 | Clear |
| 100 | Clear |
| 460 | Clear |
| Cyanide Concentration (mg/l) | |
| 1 | Turbid |
| 10 | Clear |
| 100 | Clear |

These data indicate that crotonaldehyde and cyanide are toxic to the biomass tested at levels above 1 to 10 mg/l. This concentration range is generally acknowledged as toxic to domestic microorganisms. It should be recognized that the nature and condition of the microorganism source can have an influence on the results. This is one of the reasons for the inclusion of controls as described above. The reliability of the microorganism source can be ascertained from the growth controls.

The method and apparatus described herein has been applied to actual waste water streams from the petrochemical, pulp and paper, and dye industries. The data given below in Tables V and VI were obtained from a detoxification study at a dye plant in Europe, using Method B for an evaluation of a detoxification process. The data of Table V was obtained in the manner described above in Method B on the untreated dye waste water whereas Table VI presents data obtained in the manner described above for Method B on the dye waste water after it had been subjected to a detoxification process. The apparent absorbence values were obtained with a spectrophotometer at 530 nm. The bioactivity given in the last column was calculated by dividing the apparent absorbence value of the test sample (Bottle nos. 3–10) less the value of apparent absorbence of the corresponding reagent-sample control (Bottle nos. 11, 12, 13 or 14) by the apparent absorbence value of the growth control (Bottles nos. 1 and 2).

TABLE V

| | | Untreated Dye Waste Water | | |
|---|---|---|---|---|
| Bottle No. | Identity | | Apparent Absorbence at 530 nm Read Avg. | Bioactivity (% of Control) |
| 1 | Control | Growth Control | 1.25 | |
| | | | | 1.31 |
| 2 | " | | 1.37 | |
| 3 | 3-S | | 1.10 | |
| | | | | 1.10  83 |
| 4 | 3-S | | 1.10 | |
| 5 | 2-S | | 1.10 | |
| | | | | 1.20  91 |
| 6 | 2-S | Test- Samples | 1.31 | |
| 7 | 1-S | | 0.79 | |
| | | | | 0.74  54 |
| 8 | 1-S | | 0.68 | |
| 9 | 0-S | | 0.51 | |
| | | | | 0.54  23 |

TABLE V-continued

Untreated Dye Waste Water

| Bottle No. | Identity | | Apparent Absorbence at 530 nm Read Avg. | Bioactivity (% of Control) |
|---|---|---|---|---|
| 11 | 3-CN | Reagent- Sample-Control | 0.01 | |
| 12 | 2-CN | | 0.01 | |
| 13 | 1-CN | | 0.03 | |
| 14 | 0-CN | | 0.24 | |
| 15 | Cyanide Solution | Bio-mass Background Reagent-Sample-Control | 0.01 | |
| 16 | Cyanide Solution | | 0.02 | |

TABLE VI

"Detoxified" Dye Waste Water

| Bottle No. | Identity | | Apparent Absorbence at 530 nm Read Avg. | | Bioactivity (% of Control) |
|---|---|---|---|---|---|
| 1 | Control | Growth Control | 1.64 | 1.64 | |
| 2 | " | | 1.64 | | |
| 3 | 3-S | | 1.60 | 1.55 | 94 |
| 4 | 3-S | | 1.50 | | |
| 5 | 2-S | Test- | 1.20 | 1.27 | 77* |
| 6 | 2-S | Samples | 1.34 | | |
| 7 | 1-S | | 1.43 | 1.42 | 85 |
| 8 | 1-S | | 1.42 | | |
| 9 | 0-S | | 1.27 | 1.28 | 54 |
| 10 | 0-S | | 1.30 | | |
| 11 | 3-CN | Reagent-Sample-Control | 0.01 | | |
| 12 | 2-CN | | 0.01 | | |
| 13 | 1-CN | | 0.03 | | |
| 14 | 0-CN | | 0.40 | | |
| 15 | Cyanide Solution | Background Reagent-Sample-Control | 0.01 | | |
| 16 | Cyanide Solution | | 0.02 | | |

*Probably due to calcium ions interacting with nutrients.

In addition to studying toxicity, the apparatus and method of this invention can also be used to study the effects of nutrient concentration on microbiological growth rate. In order to study the effects of nutrient concentration on the biological growth rate, it is necessary that the source of microorganisms carries no growth nutrients. This can be readily accomplished by using as the source of microorganisms the domestic sewage microorganisms that have been retained on a WHATMAN GF/C filter and washed with distilled water. The effects of nutrient concentration on biological growth rate were studied using test mixtures containing the acetate growth substrate in the amount of 5 ml of the sodium acetate solution (e), 10 mls of the nutrient-free biomass obtained by filtering domestic sewage and washing, calcium chloride at the fixed concentration of $2.5 \times 10^{-3}$ M $CaCl_2$ and the different phosphate concentrations given in Table VII. The growth control materials 7 and 8 were of the same composition as the test mixtures 1–6 but did not contain any $CaCl_2$ and the phosphate content was that given in Table VII. Since the phosphate concentration (adequate phosphorous needed for biomass growth) was varied by varying the buffer content, extreme care was taken to make certain that the pH of the test mixture was 7.2 prior to incubation. Otherwise the process of Method A was followed.

TABLE VII

| Material | | Phosphate M | pH* | Apparent Absorbence at 530 nm |
|---|---|---|---|---|
| 1 | Test mixture | $3.1 \times 10^{-2}$ | 7.5 | 0.082 |
| 2 | " | $3.1 \times 10^{-2}$ | 7.5 | 0.109 |
| 3 | " | $1.5 \times 10^{-3}$ | 7.6 | 0.063 |
| 4 | " | $1.5 \times 10^{-3}$ | 7.7 | 0.060 |
| 5 | " | $3.1 \times 10^{-4}$ | 7.8 | 0.140 |
| 6 | " | $3.1 \times 10^{-4}$ | 7.7 | 0.170 |
| 7 | Growth Control | $3.1 \times 10^{-2}$ | 7.9 | 0.170 |
| 8 | Growth Control | $3.1 \times 10^{-2}$ | 7.9 | 0.137 |

*pH after the incubation period.

The data given in Table VII reveal a variation in biomass growth with varying phosphate concentration. However, the relationship is not what would have been anticipated based on the stoichiometry of the components, i.e., the apparent absorbence dipped and the increased as the concentration of phosphate was decreased. The observed phenomenon is probably more closely associated with particle size and occluded ions rather than microorganism growth or lack of it. This illustrates the usefulness of the method and apparatus of this invention in studying the effects of nutrients and concentrations thereof on the microbiological growth rate.

What is claimed is:

1. Method of testing a material to be subjected to microorganisms to detect the presence or absence of inhibitory or toxic agents capable of inhibiting or preventing growth of said microorganisms comprising mixing a sample of said material with a liquid medium containing microorganisms, said medium being capable of supporting growth of said microorganisms; impregnating the resulting liquid mixture into a porous inert support mass capable of permitting oxygen transfer from ambient gas enveloping said mass to said mixture impregnated into it; incubating said mixture impregnated into said mass for a period of time and under conditions sufficient to promote bacterial growth therein in the absence of inhibitory or toxic agents; removing the incubated mixture from said inert support mass and filtering same through an open-pore filter; and observing the degree of turbidity, or lack of it, in the resulting filtrate.

2. Method as claimed in claim 1 wherein said liquid medium contains domestic sewage as a source of microorganisms.

3. Method as claimed in claim 1 wherein said liquid medium contains nutrients for microorganisms, a buffer and a microbiological growth substrate.

4. Method as claimed in claim 3 wherein a nutrient broth is used as the source of microorganisms.

5. Method as claimed in claim 2 wherein the source of microorganisms comprises solids obtained by filtering and washing domestic sewage.

6. Method as claimed in claim 1 wherein said material is a waste water stream from an industrial plant.

7. Method as claimed in claim 1 wherein said method is conducted in the absence of said sample of material and the degree of turbidity, or lack of it, of the resulting filtrate is compared with that resulting from conducting said method in the presence of said sample of material.

8. Method as claimed in claim 1 wherein said method is additionally conducted several times using a plurality of dilutions with water of said sample of material and the degree of turbidity, or lack of it, of each resulting filtrate is compared with that of the other resulting filtrates.

9. Method as claimed in claim 8 wherein said method is additionally conducted using water in place of said sample of material whereby a turbid filtrate results when said liquid medium is capable of supporting growth of said microorganisms.

10. Method as claimed in claim 1 wherein said method is additionally conducted and a reagent having known toxicity to said microorganism is added to said medium containing said sample, said reagent being incapable of reaction with any ingredient of said medium to form a turbid filtrate and being added in an amount sufficient to inactivate any microorganisms present therein, whereby a clear filtrate is obtained when said sample contains no component capable of reacting with any ingredient of said medium to form a turbid filtrate.

11. Method as claimed in claim 1 wherein said method is additionally conducted and a reagent having known toxicity to said microorganism is added to said medium which does not contain said sample, said reagent being incapable of reaction with any ingredient in said medium to form a turbid filtrate and being added in an amount sufficient to inactivate any microorganisms present therein whereby a clear filtrate is obtained confirming that said medium contains no ingredient capable of reacting with said reagent to form a turbid filtrate.

* * * * *

UNITED STATES PATENT OFFICE
CERTIFICATE OF CORRECTION

Patent No. 3,981,777       Dated September 21, 1976

Inventor(s) George Michael Alsop

It is certified that error appears in the above-identified patent and that said Letters Patent are hereby corrected as shown below:

In TABLE V last line of column 10 is missing:

should read:   10   0-S   0.56

Signed and Sealed this

Twenty-third Day of November 1976

[SEAL]

Attest:

RUTH C. MASON
Attesting Officer

C. MARSHALL DANN
Commissioner of Patents and Trademarks